(12) United States Patent
Rodacy et al.

(10) Patent No.: US 6,613,576 B1
(45) Date of Patent: Sep. 2, 2003

(54) FIELD KIT AND METHOD FOR TESTING FOR THE PRESENCE OF GUNSHOT RESIDUE

(75) Inventors: Philip J. Rodacy, Albuquerque, NM (US); Pamela K. Walker, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 10/047,856

(22) Filed: Jan. 15, 2002

(51) Int. Cl.[7] .............................................. G01N 21/75
(52) U.S. Cl. ...................... 436/164; 436/165; 436/174; 436/809; 436/110; 422/61; 73/35.14
(58) Field of Search ............................... 422/56, 58, 61; 436/106, 119, 127, 139, 143, 156, 164, 165, 166, 174, 177, 111, 809, 110; 73/35.14

(56) References Cited

U.S. PATENT DOCUMENTS 5,476,794 A * 12/1995 O'Brien et al. ............... 436/92

* cited by examiner

Primary Examiner—Lyle A. Alexander
(74) Attorney, Agent, or Firm—George H. Libman

(57) ABSTRACT

A field test kit for gunshot residue comprises a container having at least compartments separated by a barrier. A surface is tested by wiping it with a swab and placing the swab in a first compartment. The barrier is then breached, permitting reagent in the second compartment to flow onto the swab. The first compartment is transparent, and a color change will be observed if the reagent reacts with gunshot residue.

20 Claims, 2 Drawing Sheets

FIELD KIT AND METHOD FOR TESTING FOR THE PRESENCE OF GUNSHOT RESIDUE

The United States Government has rights in this invention pursuant to Department of Energy Contract No. DE-AC04-94AL85000 with Sandia Corporation.

CROSS REFERENCE TO RELATED APPLICATIONS (Not Applicable)

BACKGROUND OF THE INVENTION

At a shooting scene, the police frequently are confronted with a number of witnesses with conflicting stories. A rapid, reliable test for determining which of these witnesses had recently shot a gun is very useful for differentiating suspects from witnesses.

One technique used by investigators is to detect chemicals unique to a gunshot on the skin of a suspect. Gun cartridges contain a primer that ignites when it is subjected to high impact pressure by a firing pin of the gun, and a propellant (such as gunpowder) that burns when ignited by the primer. Although most of the propellant burns to produce gases that propel the bullet out the barrel, traces of unburned propellant are dispersed around the surface of the gun where they come into contact with the hands, arms, clothes, or face of the operator. The gases also propel particles of the unburned propellant onto the hands, clothes, arms, or face of the operator. If the aforementioned test detects trace chemicals from the gunpowder on a person, there is a strong presumption that person recently shot a gun, or was in close proximity to someone who did.

In one prior art field test, the paraffin test, the hands of the suspect are coated with a layer of melted paraffin. When the paraffin cools and hardens, the casts are removed and treated with a diphenylamine solution, which will color nitrates from nitroglycerine or nitrocellulose on the cast. This is a test that must be done in a laboratory, as the wax must be kept hot and melted prior to use. The chemistry of this test is discussed by Ervin Jungreis, "Spot Test Analysis, Clinical, Environmental, Forensic, and Geochemical Applications, $2^{nd}$ ed.", John Wiley & Sons, NY, 1997, Chapter 4.

The solution for this test is prepared by diluting 10 mL of concentrated sulfuric acid with 2 mL of distilled water, and then adding 0.05 grams of diphenylamine (DPA) and stirring until the DPA is dissolved. DPA is a colorless to gray solid crystal chemical that is used in rubber processing chemicals, pharmaceuticals, dyes, and as an additive for petroleum and plastic products. It has as synonyms N-phenylbenzenamine, phenylaminobenzene, big dipper, N-phenylaniline, scaldip, and anilinobenzene. It has a formula of $C_{12}H_{11}N$, and it reacts with strong acids (which is why the sulfuric acid is only slightly diluted). Both the acid and the DPA are toxic to skin, which explains why this accurate and court-approved test is conventionally performed on paraffin casts in a laboratory environment.

For another test, the skin of the suspect is swabbed with dilute hydrochloric acid. Chemicals that change colors in the presence of antimony, barium, or lead, which are other components of gun residue, are then applied to the swab.

Expray™ is an aerosol field test kit where a surface is wiped with a special test paper and sprayed with a series of chemicals. Each spray results in a color change on the paper if various explosive components are present. This test kit is not effective for gunshot residues.

A paper by John Baytos, "Field Spot-Test Kit for Explosives", Los Alamos National Laboratories, LA-12071-MS, July 1991, discloses a field kit that uses a sealed box containing swabs, chemicals, a UV light for detecting color changes, a sealable plastic envelope for protection of the swab for delivery to a laboratory for more thorough analysis. This kit is intended to detect explosives but will not detect gunshot residue. The chemical bottles and UV lamp are not as rugged as is desired for use by a law enforcement officer at a crime scene.

The aforementioned systems are not routinely used by police investigators who typically swab suspects with dilute nitric acid, seal the swab in a plastic container for transportation to a laboratory, and analyze with a scanning electron microscope (SEM) to identify the shape of inorganic particles and their chemical elements. These SEM tests are very accurate, quite expensive, and not capable of giving on-the-spot results.

Other related technology to this invention is noted:

M. Child et al., U.S. Pat. No. 5,766,962, issued Jun. 16, 1998, describes a rigid plastic container having an internal chamber containing a fluid, a place for a specimen to be placed in the container, and a viewing port. After a sample of material to be tested (such as feces) is placed in the container, the internal chamber is ruptured so fluid flows through an internal channel past the specimen to a diagnostic strip that changes color under the viewing port.

J. R. Riese, U.S. Pat. No. 4,637,061, issued Jan. 13, 1987, discloses a dual-chamber specimen and transport container. A fixative or transport solution is sealed in a lower chamber. In use, a specimen is placed in the upper chamber and the seal between chambers is undone, allowing the solution to contact the specimen. The particular seal in the '061 patent is a pair of interlocking members which make a reusable seal. Other similar packages are noted in the Background Art of the '061 patent.

It is very desirable to have an easy-to-use kit that does not involve applying a chemical to the test subject and that would provide the police at the scene with a reliable indication of which person should be treated as a suspect.

SUMMARY OF THE INVENTION

It is an object of this invention to provide a field kit for the detection of gunshot residue that is easily transportable by police, and which may quickly be used to provide an indication on the scene of whether or not a possible suspect may have recently shot a gun. To achieve the foregoing and other objects, and in accordance with the purpose of the present invention, as embodied and broadly described herein, the invention is a field test kit for detecting gunshot residue including a swab capable of being wiped by an operator upon a surface to pick up gunshot residue; a reagent for reacting with gunshot residue on said swab to provide a rapid, visible indication of the residue; and a container having first and second compartments, the second compartment containing the reagent. The first compartment has an opening for permitting the swab to be moved into the first compartment, and the opening is then sealed to prevent contamination of the device and to keep the reagent in the container. A barrier keeps the reagent out of the first compartment, but the barrier is opened by the operator to allow the reagent to pass into the first compartment.

Additional objects, advantages, and novel features of the invention will become apparent to those skilled in the art upon examination of the following description or may be learned by practice of the invention. The objects and advantages of the invention may be realized and attained as particularly pointed out in the appended claims.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

Figure 1:
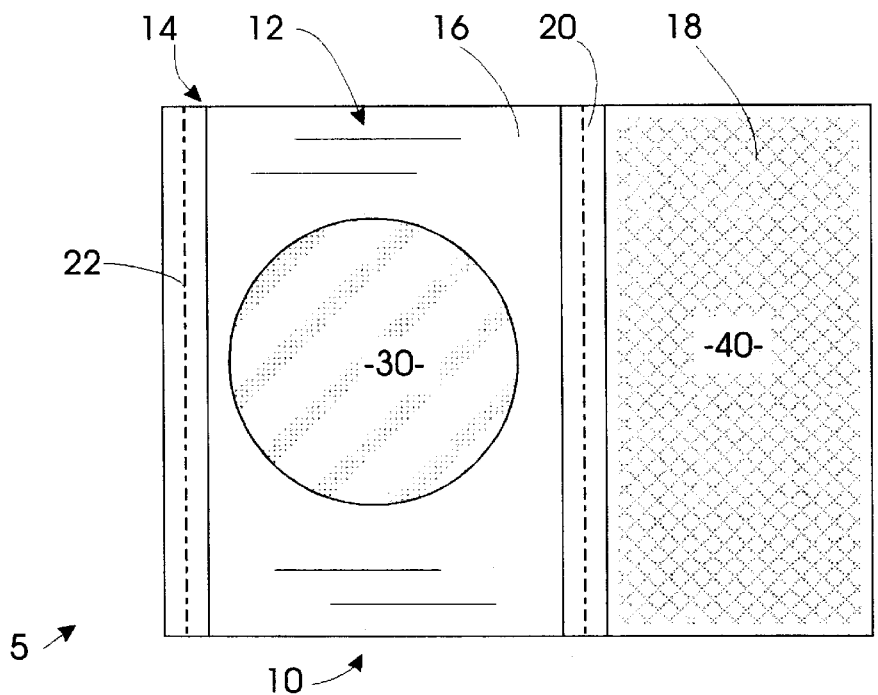
FIG. 1 shows a plan view of an embodiment of the invention.

As shown in FIG. 1, a kit 5 in accordance with this invention includes a container 10 that includes at least a pair of adjacent compartments 16, 18 that can contain a dry swab 30 and a reagent 40 as discussed hereinafter. A reagent-proof barrier 20 separates compartments 16, 18 and keeps reagent 40 from contacting swab 30. An opening 22 in compartment 16 permits swab 30 to be removed and replaced within compartment 30 as discussed hereinafter. Container 10 is preferably made of a flexible, transparent plastic sheet material such as polyethylene, and it preferably is made small enough that several kits may be carried easily in one hand.

This test kit is quite simple. Each kit provides one test. The police officer removes dry swab 30 from compartment 16 through opening 22 and rubs it over the surface to be tested for gunshot residue, which surface usually is portions of the hands of a possible suspect. The swab is then placed back into compartment 16 and opening 22 is sealed. Barrier 20 is then broken or otherwise opened, enabling reagent 40 to move from compartment 18 into compartment 16 where it contacts and covers swab 30 and any particles thereon from the suspect. Reagent 40 reacts with gunshot residue carried by swab 30 into container 10 and provides a visual indication of the presence or absence of such residue. Since container 10 is transparent, the officer can take a color picture to preserve the results of the test, which results may otherwise fade with time. If the test indicates that the possible suspect has gun residue on his skin, then the officer may take the suspect to a laboratory for other tests that are admissible in court.

Swab 30 is any material that is strong enough and with a rough enough surface to perform the function of a dry swab, attract particles, and not react to the chemicals which may be used as reagents in kit 5. A thin (about 1/64") layer of fiberglass felt proved satisfactory in tests of the invention. A cotton swab was not satisfactory as it was dissolved by the reagent, and a Teflon swab was also not satisfactory as it was so slick that it would not efficiently remove particles from the suspect nor would the color-developing solution wet the swab.

Reagent 40 may be the same acid-diphenylamine solution described above that has been utilized for nearly 70 years in the paraffin test. It turns blue when oxidized by the nitrates from residual nitroglycerine and nitrocellulose. Unlike the conventional paraffin test, the reagent remains in container 10 and is never handled by either the person applying the test or by the person being tested. Of course, other reagents could also be used that have the property of making a visual indication when placed in contact with gunshot residue on swab 30. Several such reagents are described in the aforementioned Chapter 4 of the Jungreis book.

Container 10 may be any material that does not react with the reagent or other chemicals utilized in the test and that is capable of being formed in compartments in the manner disclosed herein. Preferably, it is a flexible polyethylene or equivalent material of a type conventionally utilized in plastic bags, as such material may be designed to be strong enough for this application, yet is capable of being readily formed into the required compartments disclosed herein. A sheet of such material has relatively strong tensile strength and relatively weak compressive strength for a force applied to opposite edges. Such material may conventionally be formed into a container having opposed sides 12, 14 as shown in FIG. 1. Each compartment 16, 18 is a bag, and the two bags are separated by barrier 20 which forms part of the wall of each bag.

If container 10 is the preferred flexible plastic bag discussed above, barrier 20 may be a reusable plastic seal such as shown in U.S. Pat. No. 4,637,061. Similar seals are widely used on plastic bags for home kitchen use. Such a seal has opposed members which form a liquid-tight barrier when pressed together by an operator, or which form an opening when pulled apart by an operator. This seal would be opened when swab 30 is to be brought into contact with reagent 40. Alternatively, barrier 20 could be a membrane that is designed with a rupture strength that is weaker than any of the other surfaces of compartment 18. When pressure is applied to flexible compartment 18, the pressure exerted by reagent 40 against compartment 18 is increased, and weaker barrier 20 will fail before any external leak occurs in container. As disclosed hereinafter, other embodiments of barrier 20 are also contemplated in the practice of this invention.

Opening 22 must be able to be opened to permit swab 30 to pass freely into compartment 16 with minimal contact against opening 22, and it must seal tightly to prevent reagent 40 from escaping from container 10. Opening 22 may be as simple as a slit that opens, for removal and insertion of swab 30, and which is subsequently sealed with tape. Alternatively, it could be any resealable opening such as shown in the aforementioned Riese patent. Similar technology is widely available for use as sandwich or freezer bags.

This embodiment of the invention was tested using a 1.25 inch diameter fiberglass felt circular swab 30. To verify the sensitivity of the test, the lower limits of detection were determined by doping swabs with a laboratory solution that mimicked gunshot residue. The solution was made from 12.55% nitration nitrocellulose dissolved in acetone at a concentration of 8 parts-per-million. The solution was deposited on the swab with a microliter syringe and the acetone allowed to evaporate. Drops of the DPA/acid solution were added until the swab was completely wet (about 0.75 mL). Deposits of nitrocellulose as small as 700 nanograms turned blue when developed by the solution. Similar tests were done with a 10 ppm solution of nitroglycerine dissolved in acetonitrile and acetone. Deposits of nitroglycerine as small as 1000 nanograms produced a blue coloration. These limits are not indicative of the levels anticipated from firing a gun. Tests have shown that the levels of residue obtained from a gun is considerably higher, resulting in a high probability of detection when using the described test kit.

Field tests were also performed utilizing a series of different weapons. For all tests, each gun was cleaned prior to testing to remove any existing residue. The shooter's hands were wiped using a dry swab along the web between the thumb and forefinger, and on the palm and back of the hand to the wrist. Moistening the swab with water would enhance particle collection without significantly interfering with color development. The tests were done in summer where warm weather reduced the chemical reaction time to approximately one minute. Tests at colder temperatures (40° F.) required about two minutes for the chemical reaction.

For test A, one shooter fired one shot from each of nine guns. For test B, each gun was fired six times by a different person. The shooter's hands were swiped before each gun was fired to ensure no residual gunshot residue was on his hands and after each shot. The shooter's hands were washed between shots.

The results of these tests show that this invention provides a reasonably high probability of identifying in the field a person who recently shot a gun. The test described in this disclosure will not alter the form or composition of metallic particles, thereby allowing subsequent laboratory confirmation using SEM as described above.

Tests were also done with a reagent consisting of 0.2 grams sodium rhodizonate dissolved in water, which is a conventional reagent cited at page 81 of the Jungreis book that is used to detect barium and lead (other gunshot residues). The results of these tests were not satisfactory, as the metallic particles on the swab were so small that the color changes were very difficult to see.

It should be apparent that there are many modifications possible with this invention, as long as the concept of utilizing a swab in the field and testing the swab in the field for the presence of gunshot residue by placing it in a container and releasing a reagent stored in the container followed.

Figures 2A, 2B:
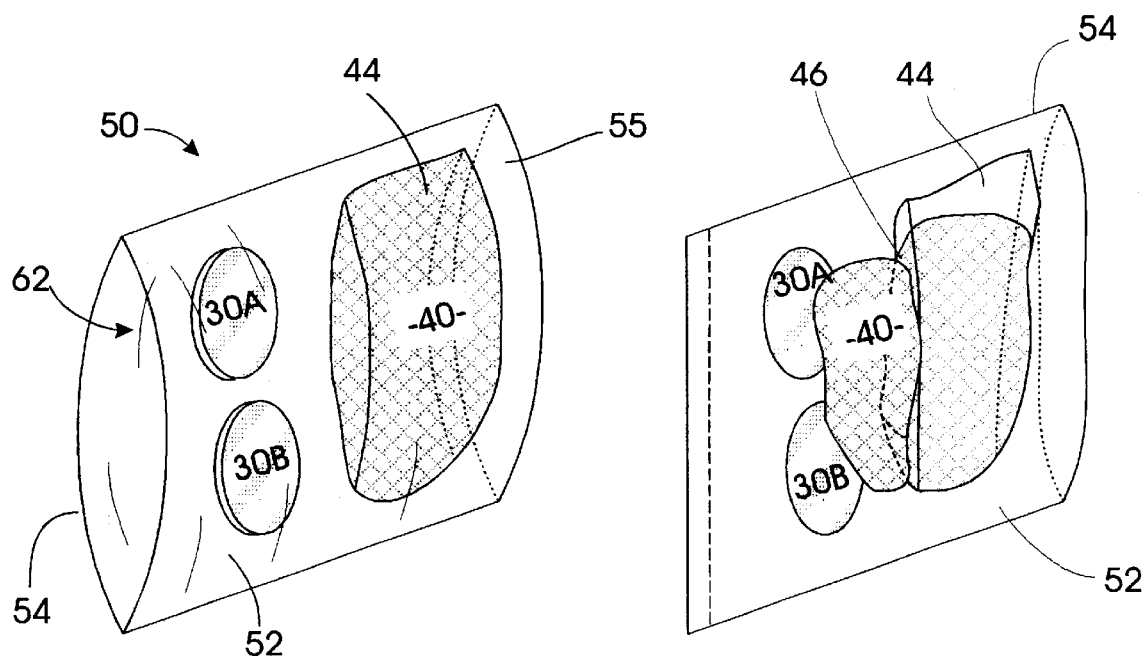
FIGS. 2A and 2B show a second embodiment of the invention.

FIG. 2A shows a second embodiment of the invention to include a container formed of opposed rigid plastic sheets 52, 54. These sheets may have a relatively strong tensile and compressive strength for a force applied to opposite edges, and flex when a force is applied normal to its surface. Container 50 may include an end piece 55 to form a fluid-tight end opposite opening 62 at the opposing end. Alternatively, end piece 55 may be omitted and the adjacent ends of sides 52, 54 may be sealed by any means.

For this embodiment, reagent 40 is contained within a pouch 44 which may be formed from plastic, metal foil, or similar materials that do not react with reagent 44, and which do not contain materials that would be indicative of gunshot residue. Pouch 44 is designed to be strong enough to retain reagent 40 during routine handling, but weak enough to fail when pressure is applied to it as discussed hereinafter; i.e., at least a portion of the surface of pouch 44 serves the function of the barrier of the first embodiment.

Swabs for the test may be packaged within container 50 or may be carried separately by the investigator. To reduce the likelihood that either the investigator is contaminating the swab or that the test has been rigged to show gunshot residue, swabs 30A and 30B have been placed within container 50 after both swabs were handled by the investigator in the same manner, but only one swab was used on the suspect.

FIG. 2B shows the container of FIG. 2A after end 54 has been sealed by any known means, including heat seal or tape. Pouch 44 has been ruptured along edge 46 to allow reagent 40 to flow within container 50 over swabs 30A and 30B. For this embodiment, the preferred means for rupturing pouch 44 is to apply inward pressure to both sides 52 and 54 of container 50. However, any other means for rupturing pouch 44 without releasing reagent 40 from container 50 is contemplated in the practice of the invention, such as providing an internal blade or point which may be moved into contact with pouch 44.

Many other variations of this invention are possible. For example, the rigid sheet material of FIG. 2 could be utilized with the two-compartment container of FIG. 1, and the pouch of FIG. 2 could be utilized with the less rigid container of FIG. 1. Furthermore, either container could be made of materials other than plastic which have the desired properties discussed herein. The portion of the container in which the swab or swabs is placed must be transparent in order that the test results may be observed without opening the container, but the portion of the container in which reagent 40 is stored may be opaque to prevent coloration of reagent 40 as a result of exposure to light.

Figure 3:
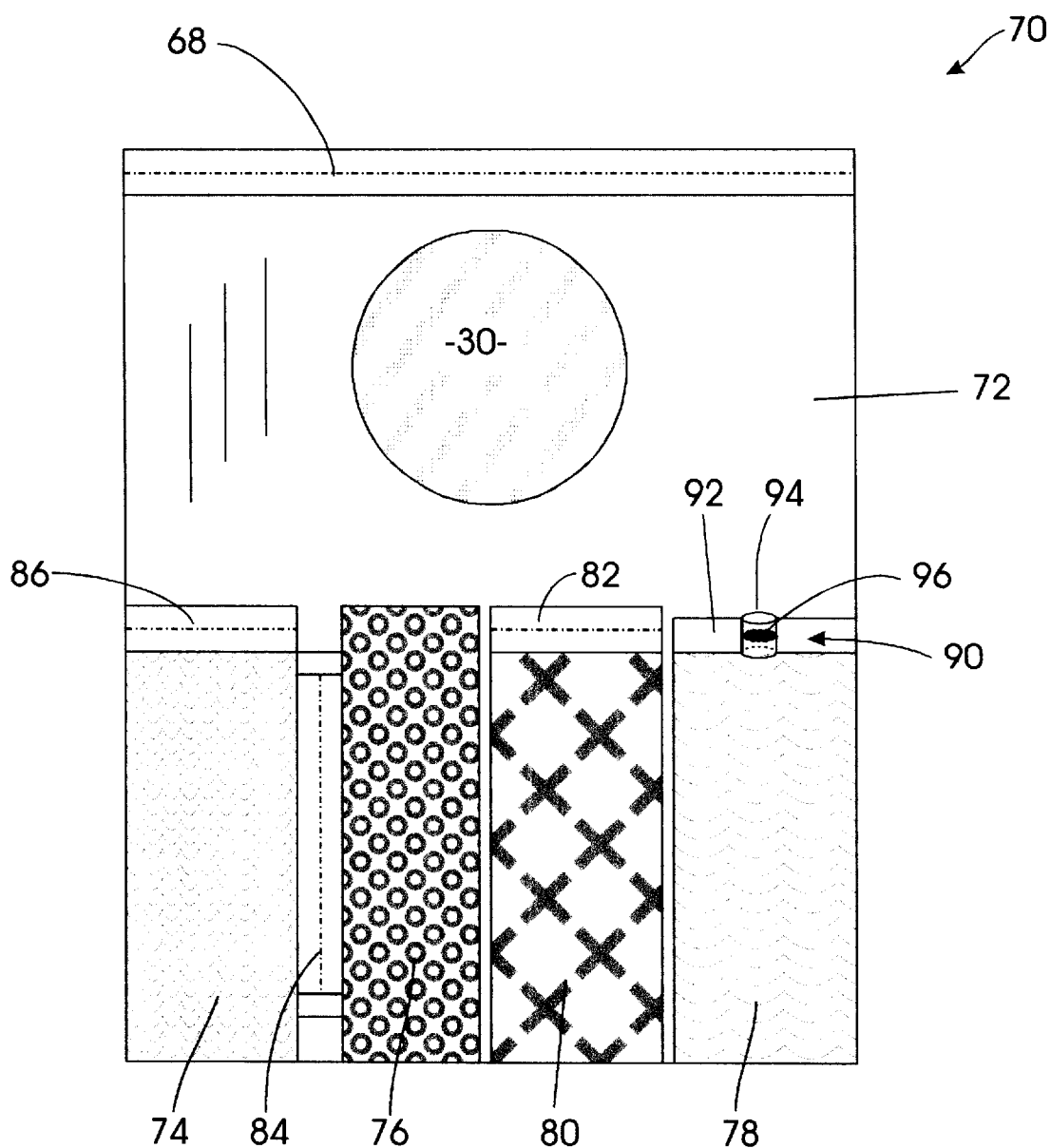
FIG. 3 shows a third embodiment of the invention.

The container may also comprise more than two compartments. FIG. 3 shows a container 70 with a compartment 72 for swab or swabs 30, and four additional compartments. If the shelf-life of reagent 40 is not sufficient, its components may be separated and mixed for use. As shown, compartment 74 contains the reagent acid and container 76 contains the reagent DPA. Immediately prior to use, seal 84 between compartments 74 and 76 is opened to permit the acid to mix with the DPA powder. Container 72 may be shaken to thoroughly mix these components. In addition, compartment 78 contains water that may be used to dampen swab 30 by opening seal 90 to compartment 72. (Tests show that a damp swab retrieves gunshot residue better than a dry swab, and water is not a hazardous material to be applied to the skin of the suspect.). After swab 30 is replaced within compartment 72 and seal 68 is closed, the reagent may be applied by opening seal 86 which controls the passage of fluid from compartment 74 to compartment 72. Lastly, to provide for a more environmentally conscious disposal of this kit, compartment 80 contains an alkaline solution such as sodium hydroxide which be applied to compartment 72 through seal 82 to neutralize the acid in compartment 72 after the test results have been obtained.

Seal 90 is a third embodiment of barrier which includes a strip 92 which may be conventionally formed by heat-sealing the opposing sides of container 70 to enclose one end of compartment 78, where strip 92 has a plugged hollow tube 94 embedded therein having one end communicating with compartment 72 and an opposed end communicating with compartment 78. Strip 92 is adhered to the outer surface of tube 94 either by a heat-sensitive adhesive that is activated when strip 92 is formed, or by forming tube 94 of a material that adheres to the heated sides of container 70. Tube 94 should be sufficiently rigid to maintain fluid flow path.

Tube 94 contains a plug 96 that seals water in container 78 until pressure is applied to container 78 that exceeds a predetermined threshold, enabling the water to flow through tube 94 into compartment 72. Plug 96 may take the form of a frangible diaphragm that covers tube 94 or it may be a wad of packing material that is pushed out of tube 94 when the water pressure in compartment 78 exceeds the threshold.

While the size of the multiple compartments 74–78 are illustrated as relatively equal, in the practice of the invention it is contemplated that the size of each compartment would be adjusted to provide an optimal amount of the material contained therein for this application. And any of the various barriers and seals disclosed herein may be utilized in any of the compartments of the invention. The particular arrangements disclosed herein are exemplary of the way that the invention may be practiced, but it is intended that the scope of the invention be defined by the appended claims.

What is claimed is:

1. A field test kit for detecting gunshot residue comprising:
   a swab capable of being wiped by an operator upon a surface to pick up gunshot residue;
   a reagent for reacting with gunshot residue on said swab to provide a visible indication of the residue, said reagent comprising sulfuric acid and diphenylamine; and
   a container comprising:
      first and second compartments, said second compartment containing said reagent;
      an opening for permitting said swab to be moved between a location outside said container and said first compartment; and
      sealing means for sealing said opening after said swab is placed in said first compartment; and
      first means for controllable keeping said reagent out of said first compartment, said first means allowing said reagent to pass into said first compartment in response to an action by an operator.

2. The field test kit of claim 1 wherein said first compartment includes an outer wall made of transparent material to permit an operator to observe color changes on said swab when said swab is in contact with said reagent.

3. The field test kit of claim 2 wherein said container is made of a flexible sheet material.

4. The field test kit of claim 3 wherein said container is made of plastic.

5. The field test kit of claim 1 wherein each compartment is a flexible bag.

6. The field test kit of claim 5 wherein said compartments are adjacent.

7. The field test kit of claim 5 wherein the action which controls said first means between said compartments is an increase in pressure applied by the operator to said second compartment.

8. The field test kit of claim 6 wherein said first means is a barrier forming a portion of each of said first and second compartments, said barrier having a rupture strength which is less than the rupture strength of the remaining portions of said second compartment.

9. The field test kit of claim 6 wherein said first means has opposed surfaces form a liquid-tight seal between said compartments and which may be pulled apart by an operator to form an opening through which said reagent will pass.

10. The field test kit of claim 6 wherein said first means comprises a hollow tube extending through said barrier from said first compartment to said second compartment, said tube including second means for blocking said tube, said second means being removed from said tube by an increase in pressure in said second compartment.

11. The field test kit of claim 10 wherein said second means comprises a plug in said tube.

12. The field test kit of claim 10 wherein said second means comprises a diaphragm extending across said tube.

13. The field test kit of claim 5 wherein said second compartment is inside said first compartment.

14. The field test kit of claim 6 further comprising a third compartment containing a neutralizer and a second barrier between said third compartment and said first compartment, said second barrier being opened by the operator to neutralize the reagent in said first compartment after the results of said test have been observed.

15. The field test kit of claim 14 further comprising a fourth compartment containing water and a third barrier between said fourth compartment and said first compartment, said third barrier being opened by the operator to wet the swab prior to wiping the surface.

16. A method for testing a surface for gunshot residue using a field test kit including a swab and a container having a first compartment having a sealable opening and a second compartment containing a reagent comprising sulfuric acid and diphenylamine, said second compartment being separated from said first compartment by a barrier, said method comprising the steps of:
   rubbing the swab over the surface;
   placing the swab in the first compartment through the opening;
   sealing the opening; and
   causing reagent to flow through the barrier to the first compartment to contact the swab;
   wherein the presence of gunshot residue on the swab is indicated by a change in color caused by the reagent.

17. The method of claim 16 wherein the reagent is a liquid that is caused to flow through the barrier by increasing the pressure on the second compartment until the barrier fails.

18. The method of claim 16 wherein one swab is rubbed over the surface and two swabs are placed in the first compartment through the opening, the second swab serving as a control to indicate whether or not the operator contaminated the swabs.

19. The field test kit of claim 1 wherein said swab comprised fiberglass.

20. The method of claim 16 wherein said swab is fiberglass and is dry when rubbed over the surface.

* * * * *